(12) United States Patent
McCarthy et al.

(10) Patent No.: US 9,155,546 B2
(45) Date of Patent: *Oct. 13, 2015

(54) SURGICAL AIMER

(75) Inventors: Gary R. McCarthy, East Bridgewater, MA (US); Michael C. Ferragamo, Foster, RI (US); Susan L. Spear, Pawtucket, RI (US)

(73) Assignee: Smith & Nephew, Inc., Memphis, TN (US)

( * ) Notice: Subject to any disclaimer, the term of this patent is extended or adjusted under 35 U.S.C. 154(b) by 802 days.

This patent is subject to a terminal disclaimer.

(21) Appl. No.: 12/578,959

(22) Filed: Oct. 14, 2009

(65) Prior Publication Data

US 2010/0042076 A1  Feb. 18, 2010

Related U.S. Application Data

(63) Continuation-in-part of application No. 12/340,896, filed on Dec. 22, 2008, now Pat. No. 8,840,604, application No. 12/578,959.

(60) Provisional application No. 61/015,907, filed on Dec. 21, 2007, provisional application No. 61/218,156, filed on Jun. 18, 2009.

(51) Int. Cl.
*A61B 17/04* (2006.01)
*A61B 17/17* (2006.01)
*A61B 17/00* (2006.01)

(52) U.S. Cl.
CPC ..... *A61B 17/1714* (2013.01); *A61B 2017/0046* (2013.01); *A61B 2017/00469* (2013.01)

(58) Field of Classification Search
CPC ................. A61B 17/1714; A61B 2017/0046; A61B 2017/00469; A61B 2017/291
USPC ........... 606/1, 80, 87, 88, 97, 98, 53, 96, 256; 600/213; 81/177.5–117.8, 450, 478, 81/484, 487, 489
See application file for complete search history.

(56) References Cited

U.S. PATENT DOCUMENTS

| | | | | |
|---|---|---|---|---|
| 2,475,896 | A * | 7/1949 | Husted | 206/259 |
| 3,672,419 | A * | 6/1972 | Fischer | 81/460 |
| 4,559,456 | A * | 12/1985 | Yamamoto et al. | 307/66 |
| 4,763,548 | A * | 8/1988 | Leibinger et al. | 81/453 |
| 5,112,335 | A * | 5/1992 | Laboureau et al. | 606/88 |

(Continued)

FOREIGN PATENT DOCUMENTS

| | | |
|---|---|---|
| GB | 2268688 A | 1/1994 |
| WO | 0249521 A1 | 6/2002 |
| WO | WO2008064211 A1 | 5/2008 |

OTHER PUBLICATIONS

International Search Report and Written Opinion for PCT/US2010/034328 Dated Jul. 29, 2010.

(Continued)

*Primary Examiner* — Lynsey Crandall
*Assistant Examiner* — Nathan J. Jenness
(74) *Attorney, Agent, or Firm* — Burns & Levinson LLP; Joseph M. Maraia

(57) ABSTRACT

The present disclosure relates to a surgical aimer including a shaft having a proximal portion and a distal portion and a handle coupled to the proximal portion of the shaft. The handle includes a mechanism for coupling the shaft to the handle and releasing the shaft from the handle.

12 Claims, 15 Drawing Sheets

(56) References Cited

U.S. PATENT DOCUMENTS

| | | | |
|---|---|---|---|
| 5,300,077 | A | 4/1994 | Howell |
| 5,320,115 | A | 6/1994 | Kenna |
| 5,320,626 | A | 6/1994 | Schmieding |
| 5,374,269 | A | 12/1994 | Rosenberg |
| 5,520,693 | A | 5/1996 | McGuire |
| 5,788,701 | A | 8/1998 | McCue |
| 5,968,050 | A | 10/1999 | Torrie |
| 6,120,511 | A | 9/2000 | Chan |
| 6,783,516 | B2 * | 8/2004 | O'Heeron et al. ............ 604/256 |
| 6,824,003 | B1 * | 11/2004 | Wong ........................ 220/254.9 |
| 7,025,770 | B2 | 4/2006 | McGuire et al. |
| 7,976,555 | B2 * | 7/2011 | Meade et al. ................ 606/148 |
| 2002/0077530 | A1 * | 6/2002 | Velikaris et al. ............ 600/213 |
| 2003/0195392 | A1 | 10/2003 | Hamel et al. |
| 2003/0229344 | A1 * | 12/2003 | Dycus et al. .................... 606/51 |
| 2004/0116843 | A1 | 6/2004 | Chan |
| 2005/0228398 | A1 | 10/2005 | Rathbun et al. |
| 2006/0106398 | A1 * | 5/2006 | Lauryssen et al. ............. 606/96 |
| 2007/0233150 | A1 * | 10/2007 | Blain et al. ..................... 606/96 |

OTHER PUBLICATIONS

Australian Examination Report No. 1 for Australian Patent Application No. 2008345557 issued on Feb. 27, 2013.

International Search Report and Written Opinion for PCT/US2008/087933 mailed May 27, 2009.

International Search Report and Written Opinion for PCT/US2010/034328 mailed Jul. 29, 2010.

International Preliminary Report on Patentability for PCT/US2010/034328 mailed Jan. 5, 2012.

\* cited by examiner

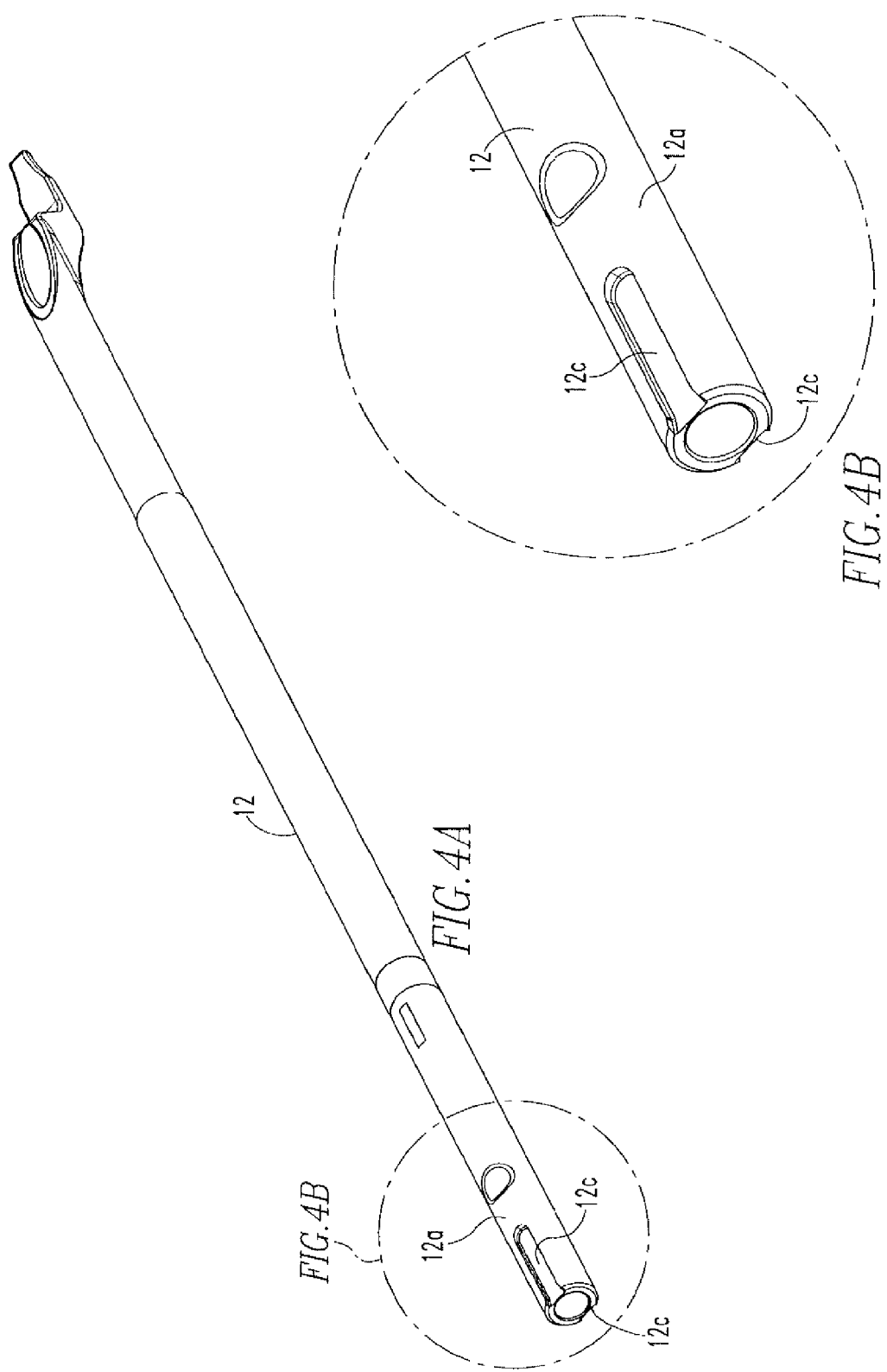

SURGICAL AIMER

CROSS-REFERENCE TO RELATED APPLICATIONS

This application is a continuation-in-part of and claims priority to U.S. patent application Ser. No. 12/340,896, which claims priority to U.S. Patent Application No. 61/015,907. This application also claims priority to U.S. Patent Application No. 61/218,156. The disclosures of all of these applications are incorporated herein by reference ill their entireties.

BACKGROUND

1. Field of Technology

The present disclosure relates to a surgical aimer, and more particularly, to a surgical aimer having a handle configured to allow a surgeon the option of an in-line or pistol grip aimer position during a ligament reconstruction procedure.

2. Related Art

When a ligament or tendon becomes detached from the bone, surgery is usually required to re-secure the ligament or tendon. Often a substitute ligament or graft is attached to the bone to facilitate re-growth and permanent attachment. The reattachment procedure involves drilling of a graft tunnel between two bones, for example, the tibia and the femur.

To achieve optimal results, it is important that the graft tunnel be drilled at a particular angle and location through the tibia and femur. Ordinarily an incision is made to access the proper area for drilling a tunnel through the tibia. A guide pin is placed through the incision and driven into the tibia. A drill is then placed over and guided by the guide pin during the drilling of the graft tunnel through the tibia.

A problem arises in locating the proper position for drilling the graft tunnel in the femur. For proper alignment of a drill guide for drilling a graft tunnel in a femur, an endoscopic drill guide including a shaft with an offset hook has been used. These drill guides allow for in-line and pistol grip positioning of the shaft relative to the handle, but the mechanisms for mounting and locking of the shaft are cumbersome.

An endoscopic drill guide that allows for easy mounting and locking of the shaft, in either an in-line or pistol grip position, is needed.

SUMMARY

In one aspect, the present disclosure relates to a surgical aimer including a shaft having a proximal portion and a distal portion and a handle coupled to the proximal portion of the shaft. The handle includes a mechanism for coupling the shaft to the handle and releasing the shaft from the handle. In an embodiment, the handle includes a first channel configured for disposal of the shaft and a second channel configured for disposal of the shaft. In another embodiment, the handle includes a first cover slidably coupled to the handle and a second cover slidably coupled to the handle. In yet another embodiment, the first cover is configured for extending over the second channel and the second cover is configured for extending over the first channel. In a further embodiment, both the first cover and the second cover include a body and an actuating portion. In yet a further embodiment, the body of the first cover includes a groove. In an embodiment, portions of the body of the first cover are configured for disposal of the portions in a channel of the mechanism when the first cover is located in first and second positions. In another embodiment, the mechanism is located within the groove of the body when the first cover is located in a third position.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings:

FIG. 4A shows an isometric view of the shaft of the surgical aimer of FIG. 1A.

FIG. 4B shows an enlarged view of the grooves of the shaft of FIG. 4A.

DETAILED DESCRIPTION OF THE EMBODIMENTS

The following description of the preferred embodiment(s) is merely exemplary in nature and is in no way intended to limit the disclosure, its application, or uses.

Figure 1A:
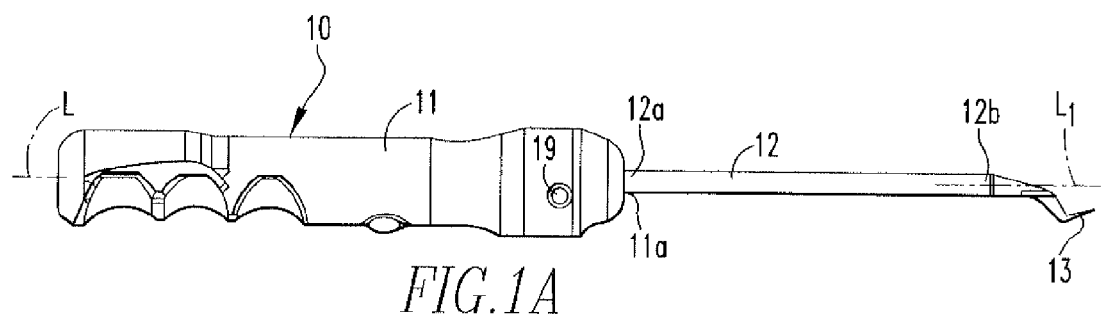
FIG. 1A shows a side view of a first embodiment of a surgical aimer of the present disclosure with the aimer located in an in-line position.
Figure 1B:
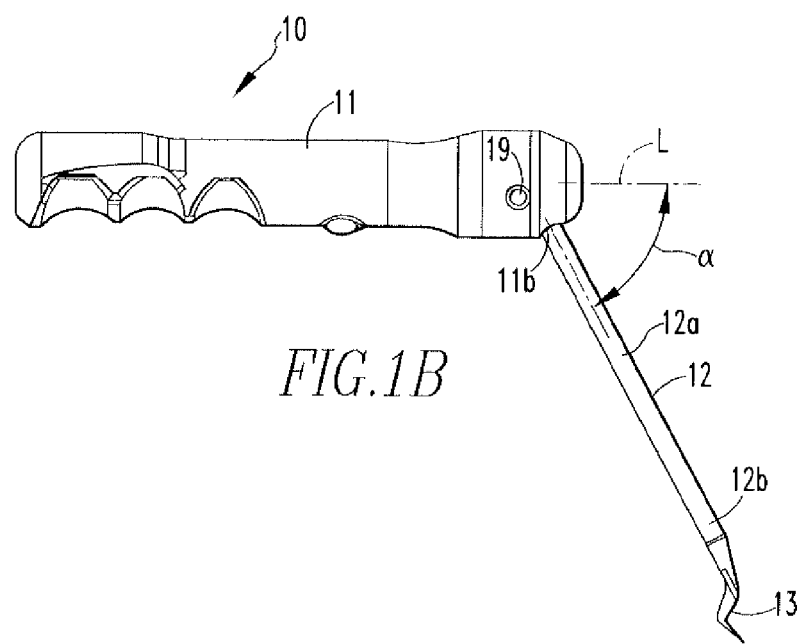
FIG. 1B shows a side view of a surgical aimer of FIG. 1A with the aimer located in a pistol grip position.

FIGS. 1A and 1B show the surgical aimer 10 of the present disclosure in all in-line position and a pistol grip position, respectively. The aimer 10 includes a handle 11 and a shaft 12 having a proximal portion 12a and a distal portion 12b, wherein the proximal portion 12a of the shaft 12 is coupled to the handle 11. In FIG. 1A, the shaft 12 is disposed within a first channel 11a that is parallel with a longitudinal axis L of tie handle 11 and in FIG. 1B, the shaft 12 is disposed within a second channel 11b that is located at an angle α relative to the longitudinal axis of the handle 11. The distal portion 12b of the shaft 12 includes a tip 13 that is offset, between about 5 mm to about 7 mm, relative to a longitudinal axis $L_1$ of the shaft 12. The handle 11 also includes a mechanism 19 for coupling the handle 11 to the shaft 12, which will be further described below.

Figure 2A:
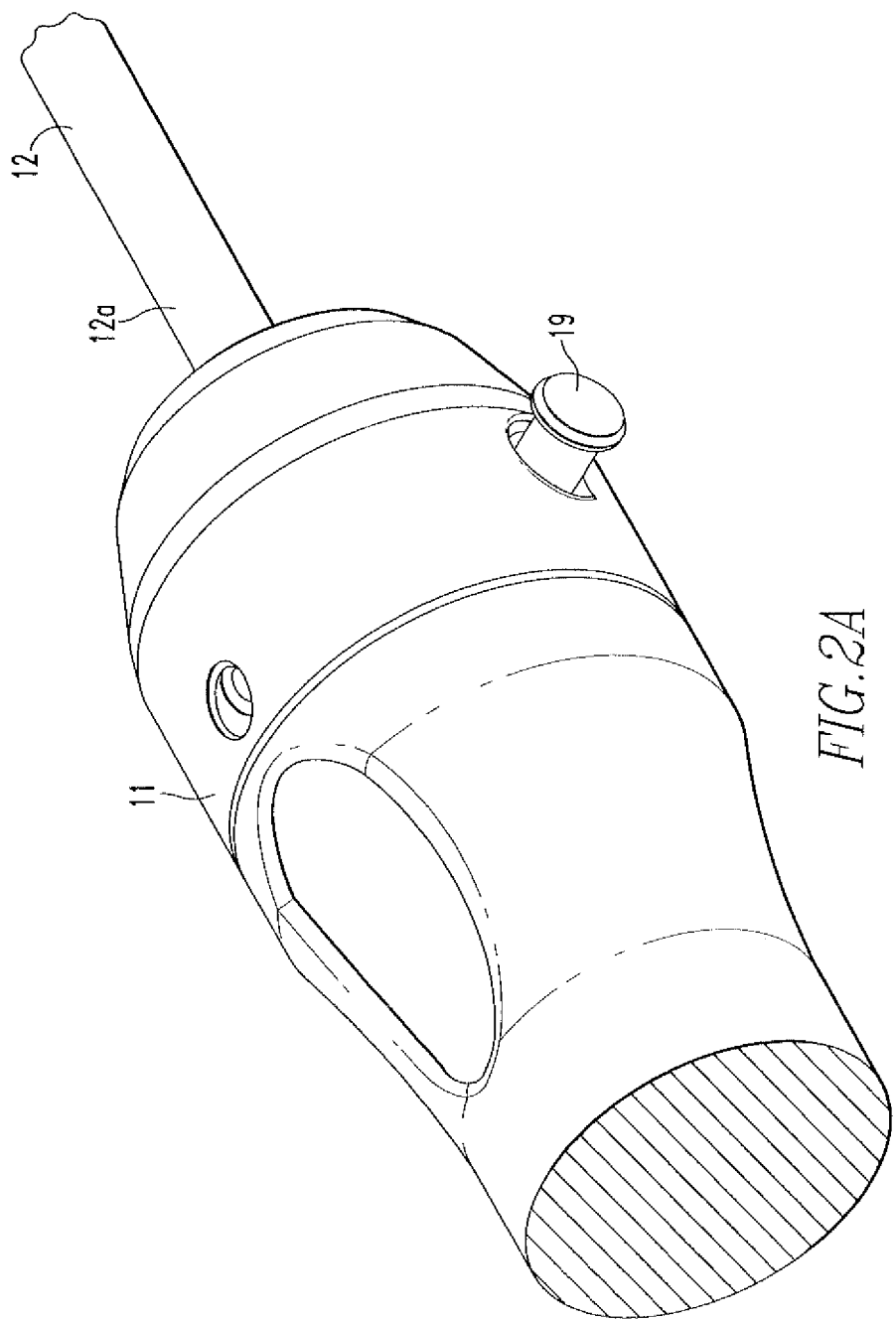
FIG. 2A shows a perspective view of the surgical aimer handle of the surgical aimer of FIG. 1A
Figure 2B:
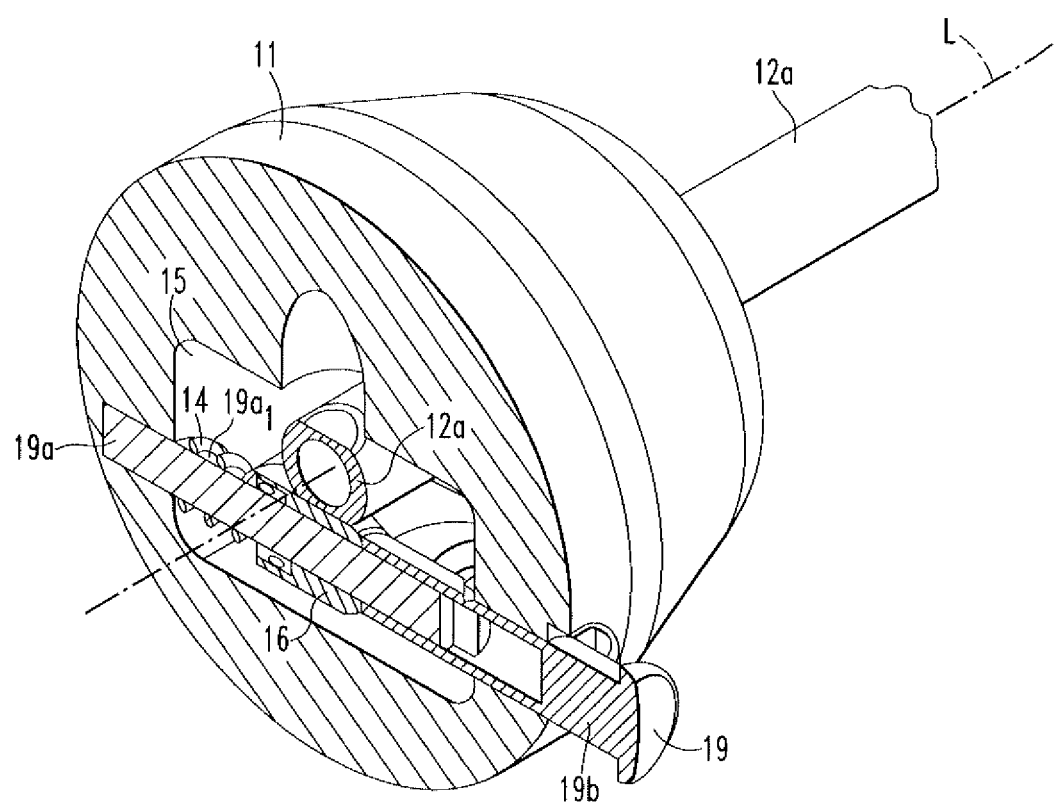
FIG. 2B shows a cross-sectional view of the surgical aimer handle of the surgical aimer of FIG. 1A.
Figure 2C:
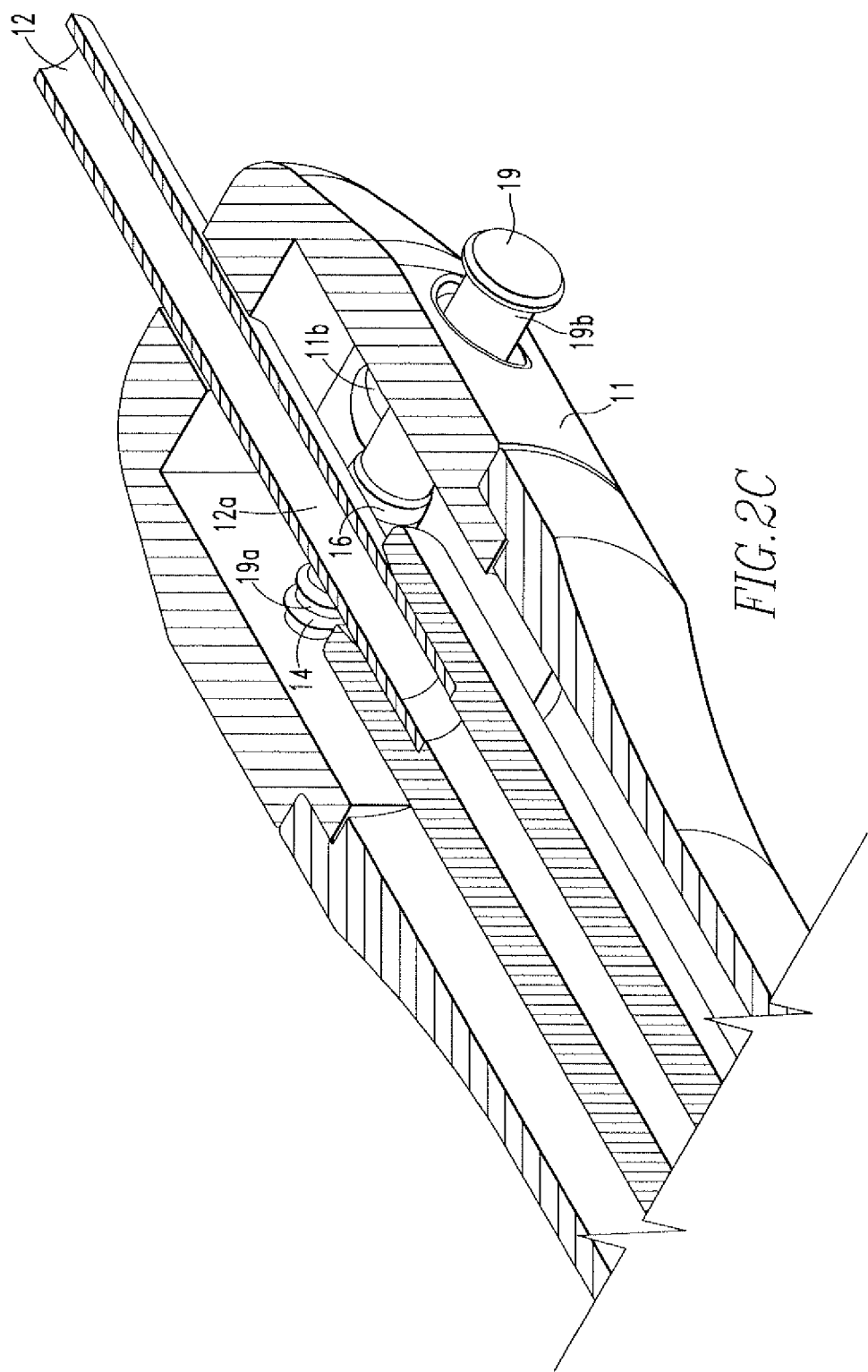
FIG. 2C shows a cross-sectional view of the surgical aimer handle and shaft of the surgical aimer of FIG. 1A.

FIGS. 2A, 2B, and 2C further show the mechanism 19 for coupling of the handle 11 to the shaft 12. As shown in FIG. 2B, the mechanism 19, which is transverse to the longitudinal axis L of the handle 11, includes a stationary member 19a and a movable member 19b slidably engaged with the stationary member 19a. A spring 14 is located on an outer surface $19a_1$ of the stationary member 19a between the movable member 19b and an inner wall 15 of the handle 11, such that the movable member 19b is spring-loaded against the stationary member 19a. The spring 14 is shown in an uncompressed state in FIGS. 2B and 2C. The movable member 19b includes a locking portion 16 that is engaged with the proximal portion 12a of the shaft 12 when the locking portion 16 is located in a first position, as shown in FIGS. 2B and 2C. However, when the mechanism 19 is activated such that the movable member compresses the spring 14 and the locking portion 16 is located in a second position, engagement between the proximal portion 12a of the shaft 12 and the locking portion 16 does not exist.

In use, the mechanist 19 is activated such that the locking portion 16 is located in a second position, as described above, the shaft 12a is disposed within the first channel 11a or the second channel 11b of the handle 11, and the mechanism 19 is then inactivated such that the locking portion 16 is located in a first position, as described above and shown in FIGS. 2B and 2C, to engage the shaft 12 and couple it to the handle 11. To uncouple the shaft 12 from the handle 11, the mechanism 19 is activated to locate the locking portion 16 in a second position, thereby disengaging the locking portion 16 from the shaft 12.

Figure 3:
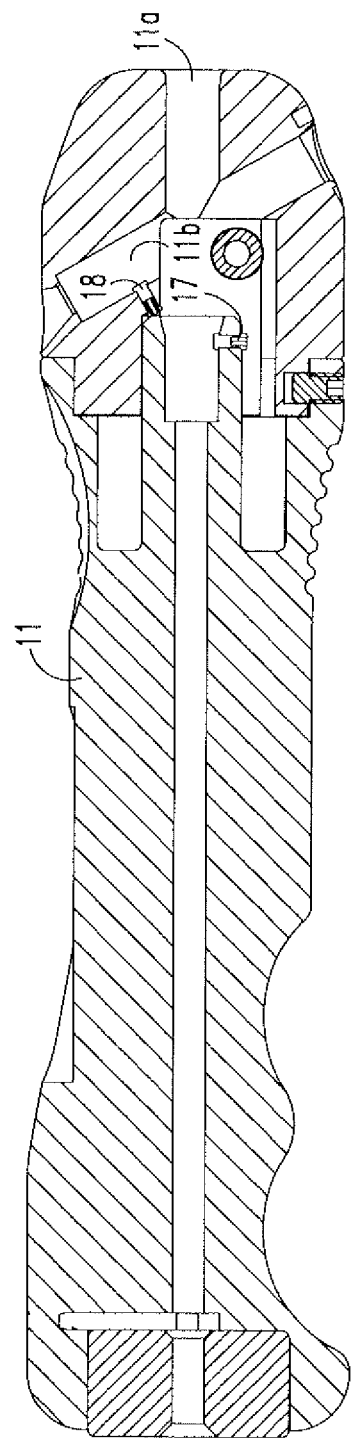
FIG. 3 shows the alignment pins of the surgical aimer handle of the surgical aimer of FIG. 1A

In addition to the locking portion 16 of the mechanism 19, FIG. 3 shows that the handle 11 also includes a first pin 17 for aligning the shaft 12 within the handle 11 when the shaft 12 is disposed within the first channel 11a and a second pin 18 for aligning the shaft 12 within the handle 11 when the shaft 12 is disposed within the second channel 11b. The pins 17,18 slide within one of two grooves 12c located on the proximal end 12a of the shaft 12, as shown in FIGS. 4A and 4B, and engage the shaft 12 as the shaft 12 is disposed within the channels 11a,11b. This engagement provides proper alignment of the shaft 12 within the channels 11a,11b and therefore the handle 11.

Figure 5A:
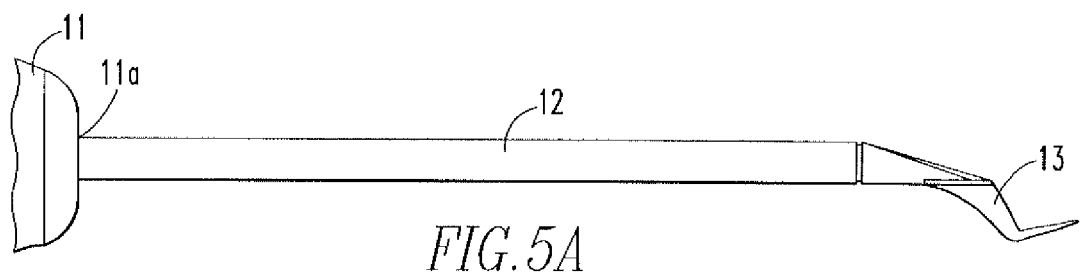
FIG. 5A shows a side view of the shaft of the surgical aimer of FIG. 1A having the tip positioned below the shaft.
Figure 5B:
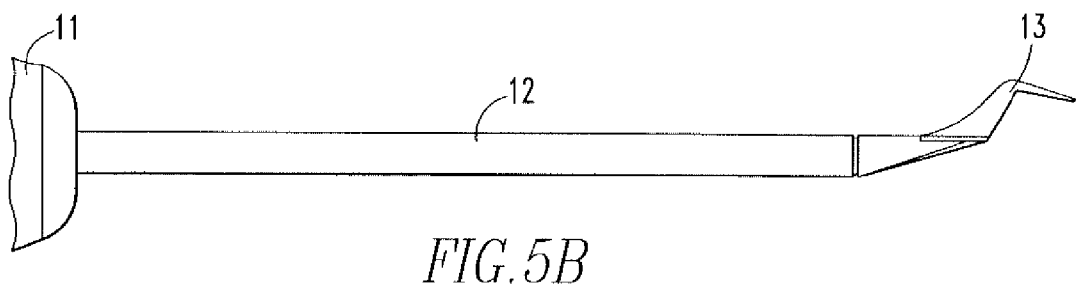
FIG. 5B shows a side view of the shaft of the surgical aimer of FIG. 1A having the tip positioned above the shaft.
Figure 6:
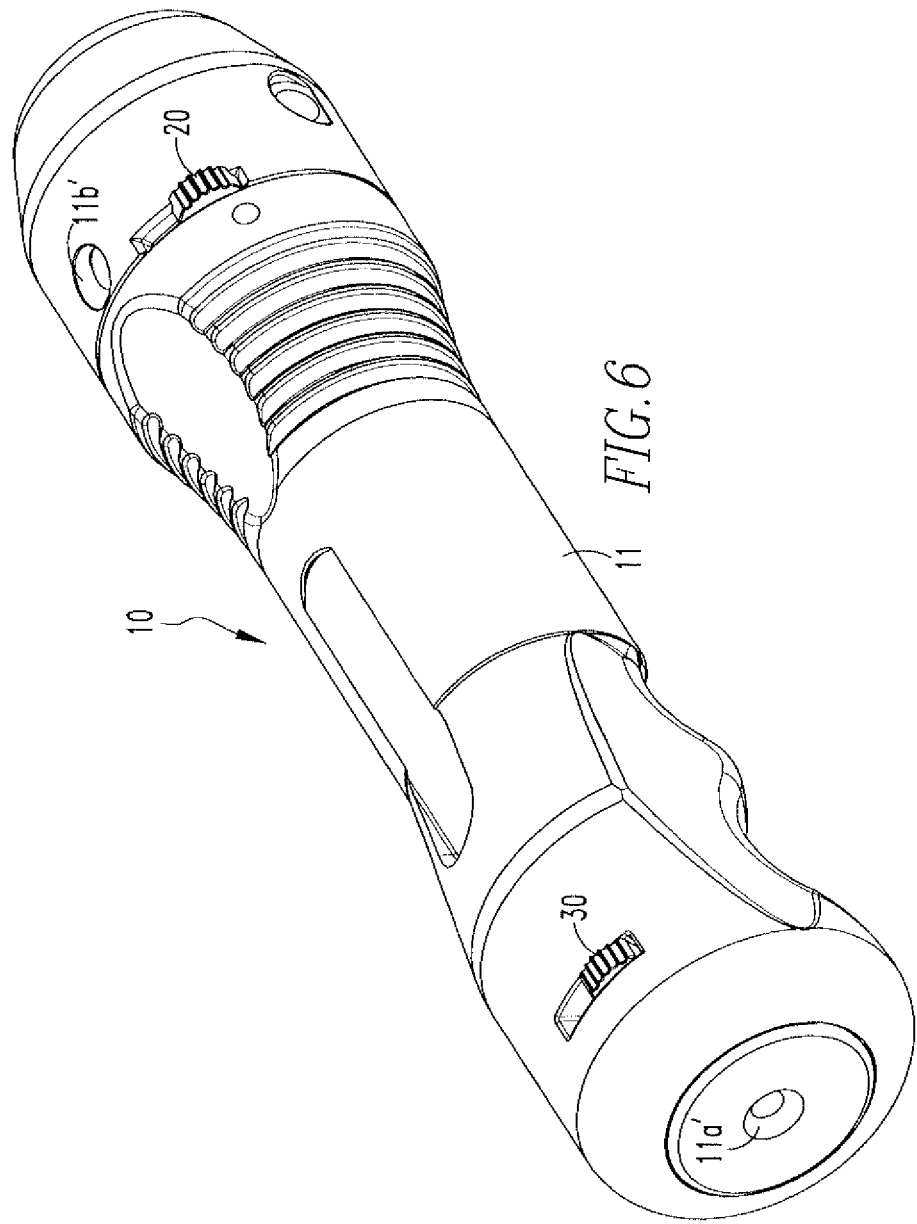
FIG. 6 shows an isometric view of the handle of a second embodiment of the surgical aimer of the present disclosure.
Figure 7:
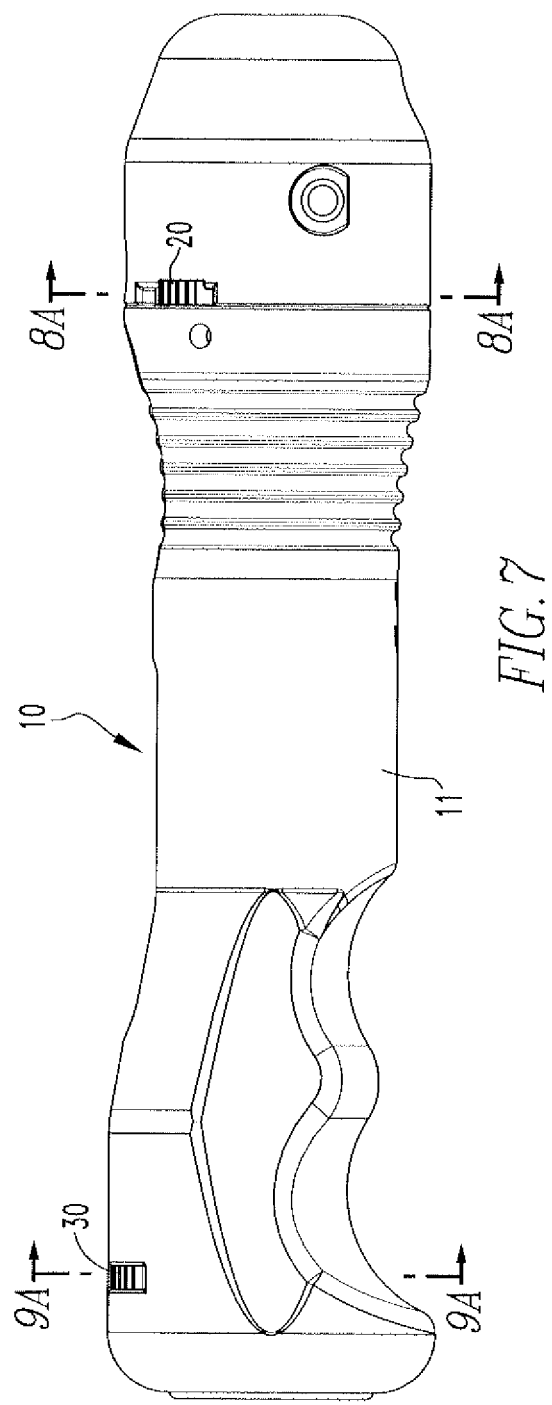
FIG. 7 shows a side view of the handle of the surgical aimer of FIG. 6.
Figure 8A:
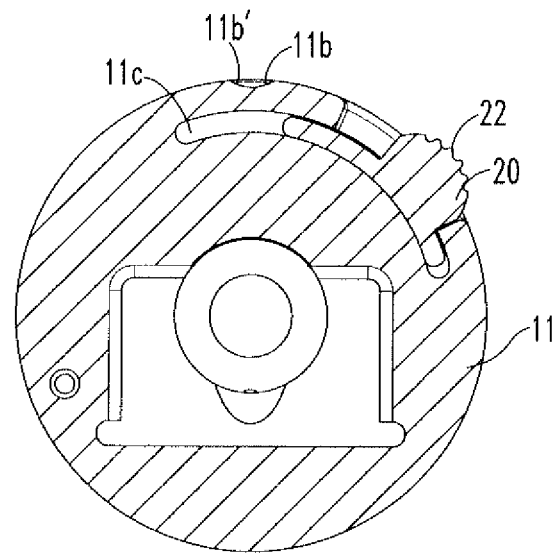
FIG. 8A shows cross-sectional view of the handle of FIG. 7 along line 8-8 with the first cover in a first position.
Figure 9A:
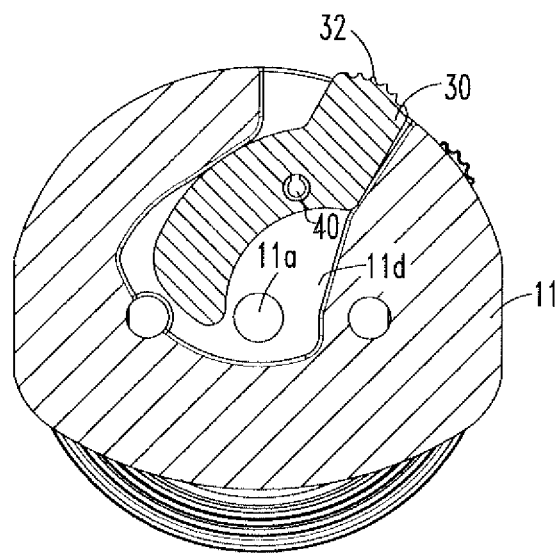
FIG. 9A shows a cross-sectional view of the handle of FIG. 7 along line 9-9 with the second cover in a first position
Figure 8B:
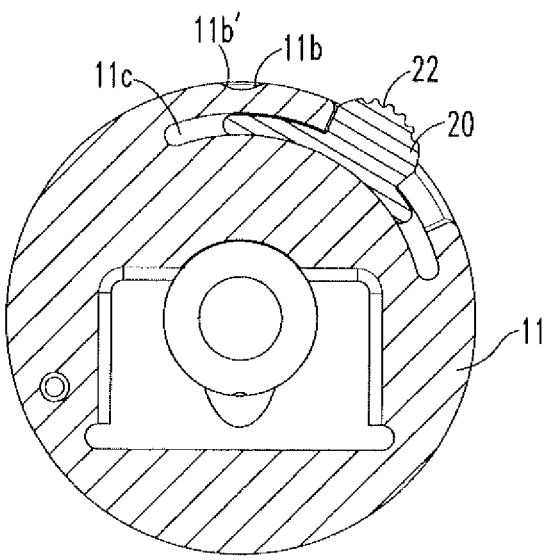
FIG. 8B shows a cross-sectional view of the handle of FIG. 7 along line 8-8 with the first cover in a second position.
Figure 9B:
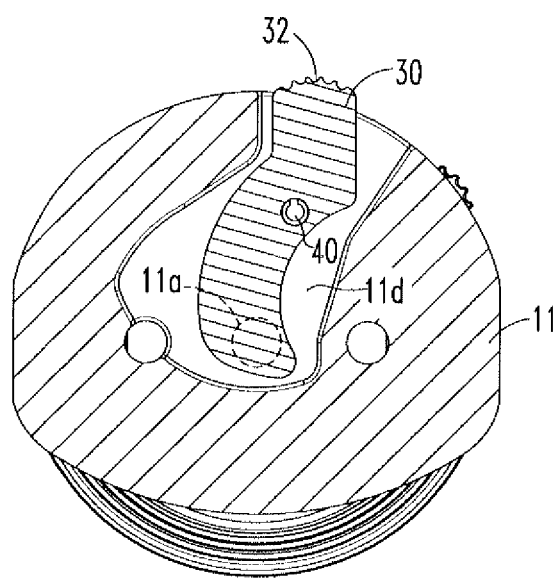
FIG. 9B shows a cross-sectional view of the handle of FIG. 7 along line 9-9 with the second cover in a second position

As shown in FIGS. 5A and 5B, the shaft 12 may also be disposed within channels 11a, 11b such that tile tip 13 is positioned below the shaft 12 or above the shaft 12, respectively. Having the tip 13 located below or above the shaft 12 is dependent on the required positioning and alignment of the shaft 12 for drilling of the graft tunnel in the femur. Regardless of the position of the tip 13, one of the two grooves 12c discussed above will engage with one of the pins 17,18 to allow for proper alignment of the shaft 12.

Figure 10:
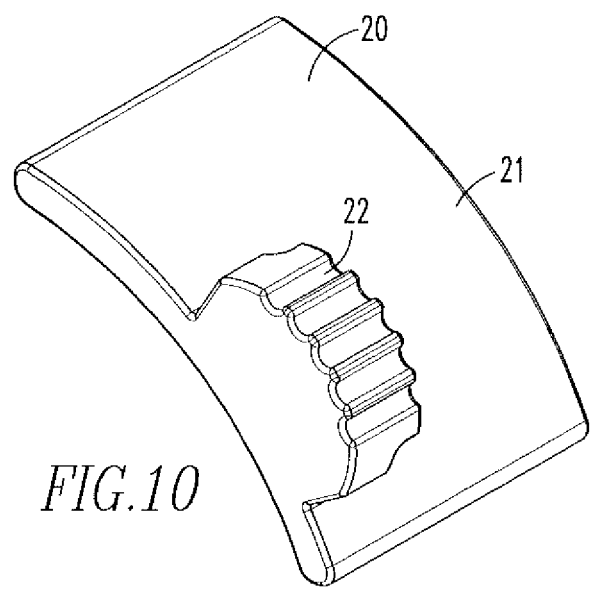
FIG. 10 shows a first cover for use with the handle of the surgical aimer of FIG. 6.
Figure 11:
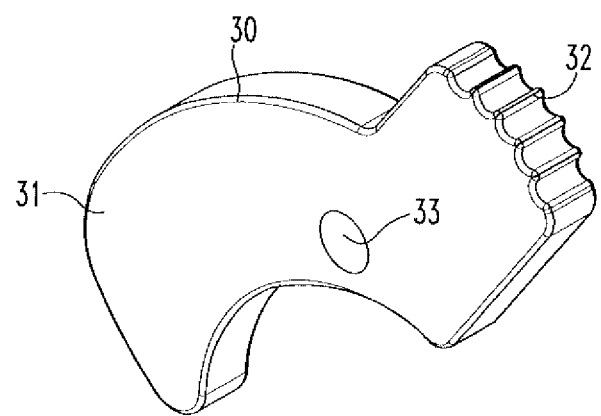
FIG. 11 shows a second cover for use with the handle of the surgical aimer of FIG. 6.

FIGS. 6-9 show a second embodiment of the surgical aimer 10 of the present disclosure. The handle 11 of the aimer 10 includes a first slidable cover 20 coupled to the handle 11 and a second slidable cover 30 coupled to the handle 11. As shown in FIGS. 10-11, the first and second covers 20,30 both include a body 21,31 having an actuating portion 22,32 and the second cover 30 includes a through hole 33 for disposition of a fixation device, as will be further described below. As shown in FIGS. 8A and 8B, the first cover 20 is housed within a first aperture 11c such that in a first position, shown in FIG. 8A, the first cover 20 doesn't extend over the second channel 11b and in a second position, shown in FIG. 8B, the first cover 20 does extend over the second channel 11b. Similarly, as shown in FIGS. 9A and 9B, the second cover 30 is housed within a second aperture 11d such that in a first position, shown in FIG. 9A, the second cover 30 doesn't extend over the first channel 11a and in a second position, shown in FIG. 9B, the second cover 30 does extend over the first channel 11a. The second cover 30 is coupled to the handle 11 via a fixation device 40, such as a screw, or other fixation device that couples the cover 30 to the handle 11, but still allows movement of the cover 30 between the first and second positions.

During use of the aimer 10 in a surgical procedure, the first and second covers 20,30 are located in their second positions in order to substantially reduce the possibility of blood and fluid from flowing out of channels 11a',11b' and thereby causing possible contamination. The user can slide the covers 20,30 between the first and second positions by applying pressure to the actuating portions 22,32, which causes the cover to move from one position to another position.

Figure 12A:
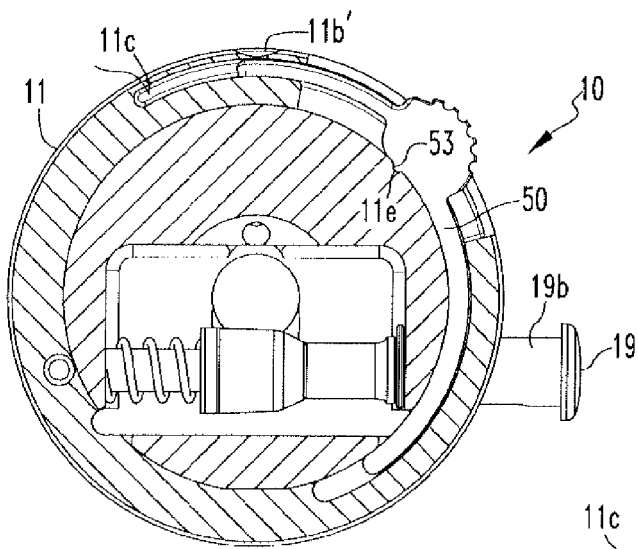
FIGS. 12A-12C show cross-sectional views of the handle on a third embodiment of the surgical aimer of the present disclosure.
Figure 12B:
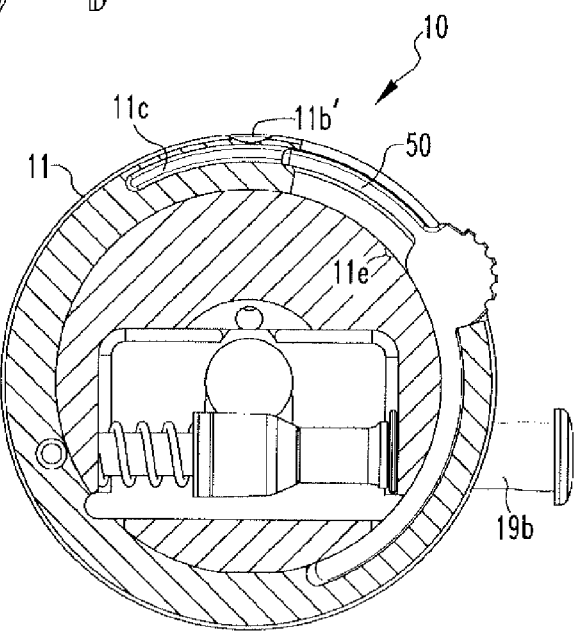
Figure 12C:
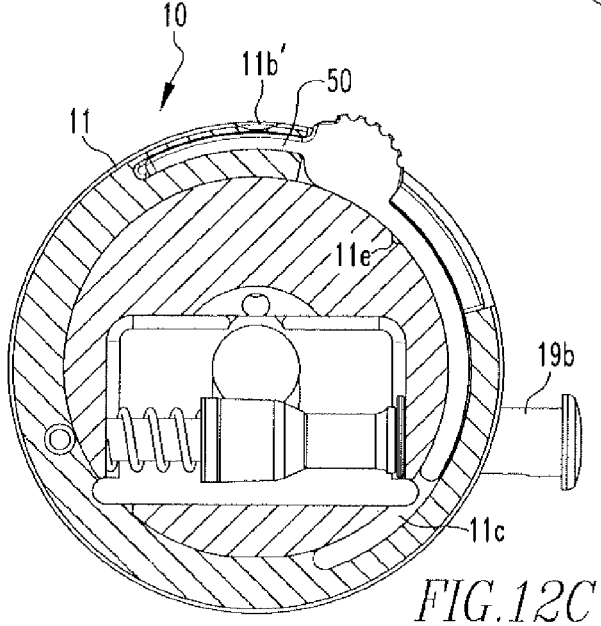
Figure 13:
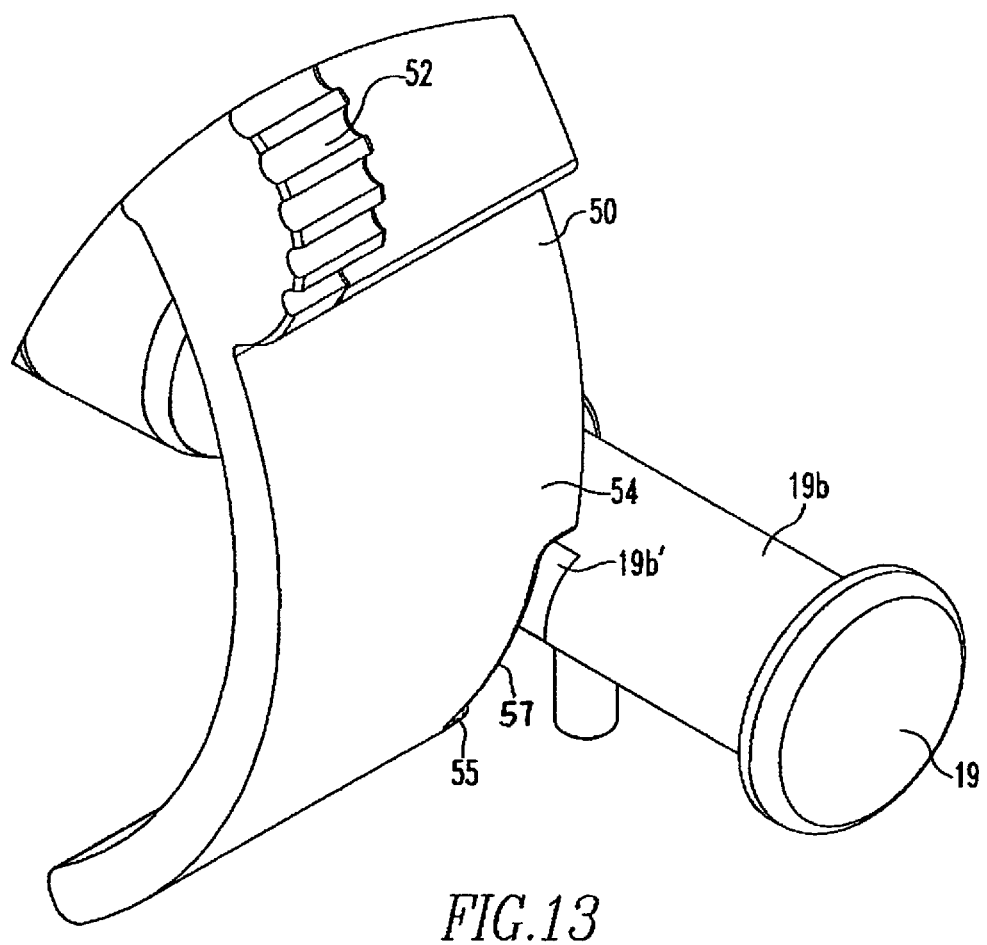
FIG. 13 shows a side view of the first cover of the handle of the third embodiment with the cover located in the position shown in FIG. 12A.
Figure 14A:
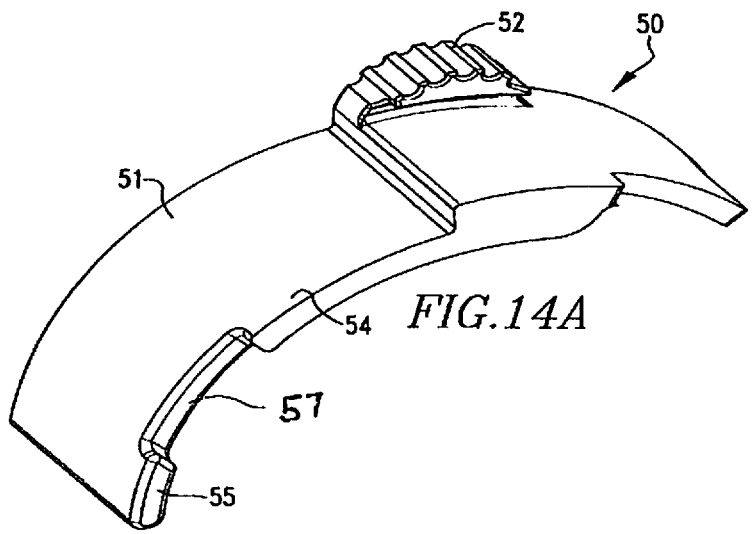
FIGS. 14A-14B show the first cover for use with the handle of FIGS. 12A-12C.
Figure 14B:
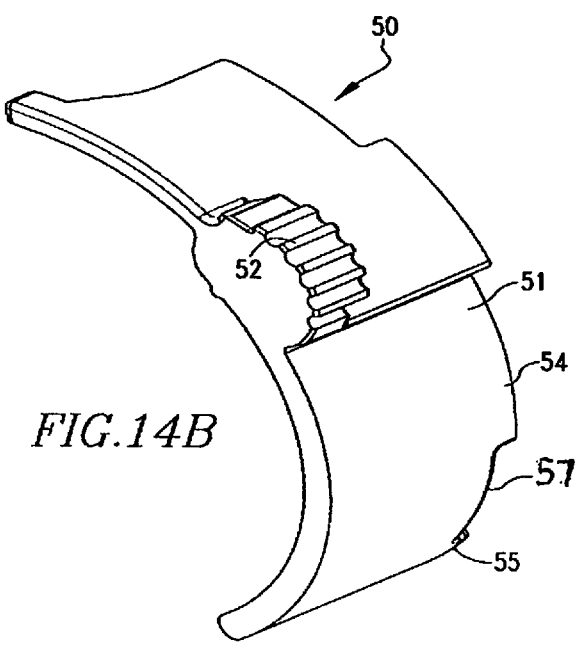

FIGS. 12A-12C show a third embodiment of the surgical aimer 10 of the present disclosure. The handle 11 of the aimer 10 includes a first slidable cover 50 coupled to the handle 11 and a second slidable cover (not shown) coupled to the handle 11. For the purposes of this embodiment, the first slidable cover 50 is different when compared to the first slidable cover 20 of FIGS. 6-11. Consequently, only the first slidable cover 50 is shown in FIGS. 12A-12C, 13, and 14A-14B. The second slidable cover of this embodiment is the same cover as the second slidable cover 30 of FIGS. 6-11. As shown in FIGS. 14A-14B, the first cover 50 includes a body 51 having an actuating portion 52 and a groove 57 for location of the movable member 19b, as will be further described below. As shown in FIGS. 12A-12C, the first cover 50 is housed within a first aperture 11c such that in a first position, shown in FIG. 12B, the first cover 50 doesn't extend over the second channel 11b, in a second position, shown in FIG. 12C, the first cover 50 does extend over the second channel 11b, and in a third position, as shown in FIG. 12A, the first cover 50 is located such that a tab 53 on the cover 50 is disposed within a divot 11e. In addition, in the third position, the cover is located such that the movable member 19b is located within the groove 57 of the cover 50, as shown in FIG. 13, and in the first and second positions, portions 54,55 of the body 51 are disposed within a channel 19b'. Consequently, when the cover 50 is in the first or second positions, actuation of the mechanism 19 is prevented and when the cover 50 is in the third position, actuation of the mechanism 19 is allowed.

During use of the aimer 10 in a surgical procedure, the first cover 50 is located in either the first or second position, depending on whether the shaft 12 is disposed within tile first channel 11a or the second channel 11b. When the shaft 12 is disposed within the first channel 11a, the first cover 50 is located in the first position, thereby preventing actuation of the mechanism 19. When the shaft 12 is disposed within the second channel 11b, the first cover 50 is located in the second position, thereby preventing actuation of the mechanism 19 and substantially reducing the possibility of blood and fluid from flowing out of opening 11b' and causing possible contamination. Prior to and after the procedure, the cover 50 may be located in the third position to allow for actuation of the mechanism 19 and subsequent disposal of the shaft 12 within the first or second channels 11a, 11b. The user can slide the cover 50 between the first, second, and third positions by applying pressure to the actuating portions 52, which causes the cover to move firm one position to another position.

The handle 11 can be used in a full range of shafts and other devices that require optional positioning. The shafts 12 may range in a variety of sizes. The aimer is 10 manufactured using medical grade materials and standard machine processes. For example, the handle 11 is made from a suitable polymer such as Radel® polyphenylsulfone (PPSU) and the shaft 12 and tip 13 are made from stainless steel. However, other medical grade materials may be used. The covers 20,30, 50 may be of a different shape than what is shown in FIGS. 10, 11, and 14A-14B. The actuating portions 22,32,52 include knurled surfaces for easier grip and movement of the covers 20,30,50. However, other surface features may be used on the portions 22,32,52.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting.

What is claimed is:

1. An orthopedic surgical aimer comprising:
   a shaft, the shaft including a proximal portion and a distal portion, the distal portion comprising a guide tip that is offset relative to a longitudinal axis of the shaft; and
   a handle having a first channel and a second channel, the first and second channels being oriented in non-parallel relation to each other, each of the channels being receptive to the proximal portion of the shaft whereby the shaft can be oriented at different angles relative to the handle as a function of the channel in which the shaft is received,
   the handle including a locking mechanism associated in common with both of the channels, the locking mechanism having a moveable member mounted for movement transversely of the channels and being selectively operable between a first position in which the shaft disposed in one of the channels will be securely and non-removably locked in one of the channels and a second, unlocked position in which the shaft may be inserted or removed from one of the channels,
   the handle including a first pin for aligning the shaft within the handle when the shaft is disposed within the first channel and a second pin for aligning the shaft within the handle when the shaft is disposed within the second channel, the first and second pins sliding within one of two grooves located on the proximal portion of the shaft and engaging the shaft as the shaft is disposed within the first and second channels.

2. The orthopedic surgical aimer of claim 1 wherein each of the channels has an opening to receive the shaft and wherein the handle includes a first cover slidably coupled to the handle to cover the opening to one of the channels and a second cover slidably coupled to the handle to cover the opening of the other channel.

3. The orthopedic surgical aimer of claim 2 wherein the first cover is configured for extending over the opening of the second channel and the second cover is configured for extending over the opening of the first channel.

4. The orthopedic surgical aimer of claim 2 wherein both the first cover and the second cover include a body and an actuating portion.

5. The orthopedic surgical aimer of claim 4 wherein the body of the first cover includes a groove.

6. The orthopedic surgical aimer of claim 1 wherein the locking mechanism further comprises:
   the moveable member having an inner portion disposed within the handle and an outer portion extending out of the handle, the moveable member being selectively moveable between a first position and a second position; and
   the inner portion having a locking portion moveable with the moveable member between a first position engageable with the proximal portion of the shaft disposed in either of the channels to securely non-removably lock the shaft in either of the channels and a second position in which the locking portion is in a non-locking position enabling removal or insertion of the shaft out of or into either of the channels.

7. The orthopedic surgical aimer of claim 6 further comprising means biasing the moveable member toward its first position.

8. The orthopedic surgical aimer of claim 7 wherein the biasing means comprises a spring.

9. The orthopedic surgical aimer of claim 7 wherein the handle has an axis and the moveable member is moveable transversely to the handle axis.

10. The orthopedic surgical aimer of claim 6 wherein the handle has an axis and the moveable member is moveable transversely to the handle axis.

11. The orthopedic surgical aimer of claim 1 wherein the proximal end of the shaft is receivable in either channel in one of a plurality of angular orientations about the axis of the shaft, whereby the guide tip may be oriented in selected orientations with respect to the handle.

12. The orthopedic surgical aimer of claim 11 wherein the plurality of angular orientations comprises two that are disposed 180° apart about the axis of the shaft.

* * * * *